US010767934B2

(12) United States Patent
Yoshinoya et al.

(10) Patent No.: US 10,767,934 B2
(45) Date of Patent: Sep. 8, 2020

(54) REACTOR

(71) Applicant: IHI CORPORATION, Tokyo (JP)

(72) Inventors: Takuya Yoshinoya, Tokyo (JP);
Nobuyuki Honma, Tokyo (JP)

(73) Assignee: IHI CORPORATION, Tokyo (JP)

(*) Notice: Subject to any disclaimer, the term of this patent is extended or adjusted under 35 U.S.C. 154(b) by 129 days.

(21) Appl. No.: 16/047,035

(22) Filed: Jul. 27, 2018

(65) Prior Publication Data

US 2018/0372415 A1 Dec. 27, 2018

Related U.S. Application Data

(63) Continuation of application No. PCT/JP2017/008229, filed on Mar. 2, 2017.

(30) Foreign Application Priority Data

Mar. 3, 2016 (JP) .................................. 2016-041079

(51) Int. Cl.
*F25D 3/12* (2006.01)
*F28D 9/00* (2006.01)
(Continued)

(52) U.S. Cl.
CPC .......... *F28D 9/0075* (2013.01); *B01J 19/248* (2013.01); *B01J 19/249* (2013.01); *B01J 35/02* (2013.01);
(Continued)

(58) Field of Classification Search
CPC ........ F28D 9/0075; F28D 9/0062; F28F 9/02; F28F 3/025; F28F 3/06; F28F 3/08;
(Continued)

(56) References Cited

U.S. PATENT DOCUMENTS 5,015,446 A 5/1991 Trujillo
10,118,148 B2 * 11/2018 Sakakura .............. B01J 19/249
(Continued)

FOREIGN PATENT DOCUMENTS

CA 2 833 055 A1 5/2014
CN 103816840 A 5/2014
(Continued)

OTHER PUBLICATIONS

Japan Patent Office, "Notice of Reasons for Refusal", issued in Japanese Patent Application No. 2016-041079, which is a Japanese counterpart of U.S. Appl. No. 16/047,035, dated Feb. 12, 2020, 3 pages.
(Continued)

*Primary Examiner* — Claire E Rojohn, III

(57) ABSTRACT

A reactor includes: a heat exchange body including a heat medium channel through which the heat medium flows and a reaction channel through which the reaction fluid flows; at least one structured catalyst supporting a catalyst for promoting the reaction of the reaction fluid and removably installed in the reaction channel; and a holding member including an extending part extending in a direction conforming to an extending direction of the reaction channel and capable of engaging with the at least one structured catalyst, and regulating parts provided in the extending part to regulate a movement of the at least one structured catalyst in the extending direction of the extending part, wherein the holding member is inserted and removed with respect to the reaction channel while holding the structured catalyst.

10 Claims, 7 Drawing Sheets

(51) Int. Cl.
*F28F 3/06* (2006.01)
*F28F 21/08* (2006.01)
*B01J 19/24* (2006.01)
*F28F 3/02* (2006.01)
*B01J 35/02* (2006.01)
*F28F 3/08* (2006.01)
*F28D 21/00* (2006.01)
*F28F 9/02* (2006.01)
*C07B 61/00* (2006.01)
*C07C 9/02* (2006.01)

(52) U.S. Cl.
CPC ............ *F28D 9/0062* (2013.01); *F28F 3/025* (2013.01); *F28F 3/06* (2013.01); *F28F 3/08* (2013.01); *F28F 21/083* (2013.01); *F28F 21/087* (2013.01); *B01J 2219/00096* (2013.01); *B01J 2219/2453* (2013.01); *B01J 2219/2458* (2013.01); *B01J 2219/2462* (2013.01); *B01J 2219/2471* (2013.01); *B01J 2219/2479* (2013.01); *B01J 2219/2498* (2013.01); *C07B 61/00* (2013.01); *C07C 9/02* (2013.01); *F28D 2021/0022* (2013.01); *F28F 9/02* (2013.01)

(58) Field of Classification Search
CPC ........ B01J 19/248; B01J 19/249; B01J 35/02; B01J 2219/00096; B01J 2219/2453; B01J 2219/2458; B01J 2219/2462; B01J 2219/2471; B01J 2219/2479; B01J 2219/2498; C07C 9/02
USPC ....................................................... 165/166
See application file for complete search history.

(56) References Cited

U.S. PATENT DOCUMENTS

| | | |
|---|---|---|
| 2001/0026782 A1 | 10/2001 | Wang et al. |
| 2010/0143215 A1 | 6/2010 | Caze et al. |
| 2011/0114084 A1* | 5/2011 | Hagg ............... F24F 12/006 126/678 |
| 2011/0146941 A1* | 6/2011 | Benoit ............... F28D 9/0062 165/11.1 |
| 2012/0195801 A1* | 8/2012 | Whittenberger ...... B01J 8/0242 422/129 |
| 2012/0237415 A1 | 9/2012 | Ramos et al. |
| 2013/0202498 A1* | 8/2013 | Maxted ................ C01B 3/384 422/219 |
| 2014/0262144 A1* | 9/2014 | Erb ...................... F28F 9/001 165/60 |
| 2015/0336077 A1 | 11/2015 | Kamata et al. |
| 2016/0107138 A1* | 4/2016 | Kamata ............... B01F 5/0082 422/198 |
| 2016/0144336 A1* | 5/2016 | Hamada .............. B01J 19/249 422/601 |
| 2016/0341493 A1* | 11/2016 | Dinulescu ........... F28D 9/0062 |
| 2018/0318786 A1* | 11/2018 | Yano .................. B01J 19/2425 |
| 2019/0101339 A1* | 4/2019 | Ling ................... F28D 9/0025 |
| 2019/0219344 A1* | 7/2019 | Yamamoto .......... F28F 9/027 |
| 2019/0226765 A1* | 7/2019 | Xu ..................... F25J 3/04466 |
| 2019/0310026 A1* | 10/2019 | Chopard .............. F28F 9/001 |
| 2019/0310030 A1* | 10/2019 | Disori .................. F28F 3/06 |
| 2019/0366876 A1* | 12/2019 | Cheadle ............... B60L 58/26 |
| 2020/0108474 A1* | 4/2020 | Thresher ............. F28D 9/0062 |

FOREIGN PATENT DOCUMENTS

| | | |
|---|---|---|
| CN | 104707540 A | 6/2015 |
| EP | 3 415 231 A1 | 12/2018 |
| JP | S53-025264 A | 3/1978 |
| JP | S54-046919 U1 | 3/1979 |
| JP | H06-052923 U | 7/1994 |
| JP | 2000-154001 A | 6/2000 |
| JP | 2007-237044 A | 9/2007 |
| JP | 2007-244944 A | 9/2007 |
| JP | 2010-207756 A | 9/2010 |
| JP | 2013-540052 A | 10/2013 |
| JP | 2014-514955 A | 6/2014 |
| JP | 2014-144418 A | 8/2014 |
| JP | 2014-151245 A | 8/2014 |
| JP | 2015-223582 A | 12/2015 |
| WO | 2001/012312 A2 | 2/2001 |
| WO | 2013/001275 A2 | 1/2013 |
| WO | 2014/208444 A1 | 12/2014 |
| WO | 2014/208646 A1 | 12/2014 |
| WO | 2015/037597 A1 | 3/2015 |

OTHER PUBLICATIONS

The State Intellectual Property Office of People's Republic of China, "First Office Action", issued in Chinese Patent Application No. 201780007688.8, which is a Chinese counterpart of U.S. Appl. No. 16/047,035, dated Sep. 16, 2019, 6 pages.

European Patent Office, "Extended European Search Report," issued in European Patent Application No. 17 760 117.6, which is a European counterpart of U.S. Appl. No. 16/047,035, dated Jun. 27, 2019, 8 pages.

* cited by examiner

REACTOR

CROSS REFERENCE TO RELATED APPLICATIONS

This application is a continuation application of International Application No. PCT/JP2017/008229, filed on Mar. 2, 2017, which claims priority to Japanese Patent Application No. 2016-041079, filed on Mar. 3, 2016, the entire contents of which are incorporated by reference herein.

BACKGROUND

1. Technical Field

The present disclosure relates to a heat exchanger-type reactor.

2. Description of the Related Art

Heat exchanger-type reactors are known as a chemical reaction apparatus which heats or cools a reaction fluid in a gas or liquid state containing a reaction raw material as a reactant so as to promote a reaction of the reactant. Such a reactor is provided with reaction channels through which a reaction fluid flows and heat medium channels through which a heat medium flows, in which heat exchange between the reaction fluid and the heat medium proceeds during a period from supplying the reaction fluid and the heat medium from the respective inlets to draining the reaction fluid and the heat medium from the respective outlets. The reaction channels and the heat medium channels provided in the reactor are each branched into a plurality of channels so as to increase the heat transfer area to facilitate the heat exchange. A catalyst is provided in the respective reaction channels, so that the chemical reaction is efficiently promoted in the respective reaction channels owing to the effect of the catalyst. Japanese Unexamined Patent Application Publication No. 2014-144418 (Patent Literature 1) discloses a reactor including reaction channels including a plurality of branch channels arranged in parallel and in layers, and catalyst plates installed in the respective branch channels.

SUMMARY

A structured catalyst used in the reactor as disclosed in Patent Literature 1 typically entirely extends in one direction, and is obtained such that active metal serving as a catalyst is supported on a metal plate having a corrugated shape in cross section. Such a structured catalyst is removably installed in the respective branch channels of the reaction channels, more particularly, positioned and installed in each reaction channel before the reaction processing starts, and removed and replaced as appropriate when the reaction amount or reaction time exceeds a predetermined level, for example. When the structured catalyst used is shorter than the length of the branch channels, a plurality of structured catalysts aligned in series may be installed in one branch channel. However, it requires a lot of work to remove all of the structured catalysts once installed in series in the respective branch channels. The problem with the removal is significant particularly when the branch channels are relatively small in cross section or the number of the branch channels is large, or when the installation or removal of the structured catalysts is possible only either from the upstream side or the downstream side of the branch channels for the structural reasons in the reactor.

When the reactor has a complex structure in which the branch channels arranged in parallel are stacked in layers as disclosed in Patent Literature 1, the operator needs to preliminarily align the structured catalysts one by one to some extent before installing the structured catalysts in the respective branch channels. It therefore takes much time to position the plural structured catalysts to be aligned in series in each branch channel.

Further, the structured catalysts are not tightly fixed to inner walls of the branch channels. As a result, the structured catalysts may be displaced from a predetermined position in the respective reaction channels because of a flowing pressure of a fluid during the reaction processing to result in a failure in exhibiting preferred reaction efficiency.

An object of the present disclosure is to provide a reactor having a structure capable of facilitating installation and removal of structured catalysts with respect to reaction channels and ensuring positional stability of the structured catalysts in the reaction channels.

An aspect of the present disclosure is a reactor using heat exchange between a heat medium and a reaction fluid to cause a reaction of the reaction fluid to proceed, the reactor including: a heat exchange body including a heat medium channel through which the heat medium flows and a reaction channel through which the reaction fluid flows; at least one structured catalyst supporting a catalyst for promoting the reaction of the reaction fluid and removably installed in the reaction channel; and a holding member including an extending part extending in a direction conforming to an extending direction of the reaction channel and capable of engaging with the at least one structured catalyst, and regulating parts provided in the extending part to regulate a movement of the at least one structured catalyst in the extending direction of the extending part, the holding member being inserted and removed with respect to the reaction channel while holding the at least one structured catalyst.

DESCRIPTION OF THE EMBODIMENTS

Figure 1A:
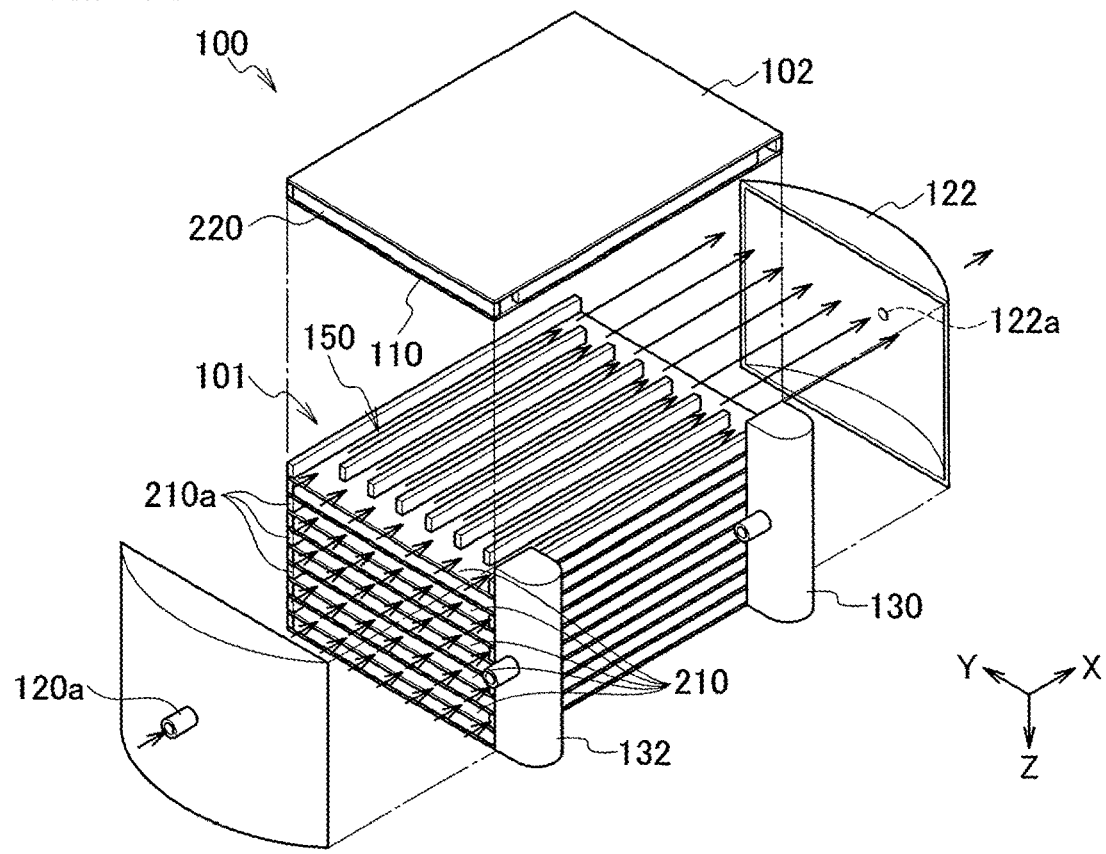
FIG. 1A is a view showing a structure of a reactor according to an embodiment of the present disclosure and illustrating a flow of a reaction fluid.

Embodiments according to the present disclosure will be described in detail below with reference to the drawings. The following dimensions, materials, and specific numerical values described in the embodiments are shown for illustration purposes only, and the present disclosure is not limited thereto unless otherwise specified. The elements having substantially the same functions and structures illustrated in the Specification and the drawings are designated by the same reference numerals, and overlapping explanations are not repeated below. The elements described below but not related directly to the present disclosure are not shown in the drawings. In the following explanations of the drawings, a vertical direction is defined as a Z-axis, an extending direction of reaction channels 150 described below on a plane perpendicular to the Z-axis is defined as an X-axis, and a direction perpendicular to the X-axis is defined as a Y-axis.

First Embodiment

Figure 1B:
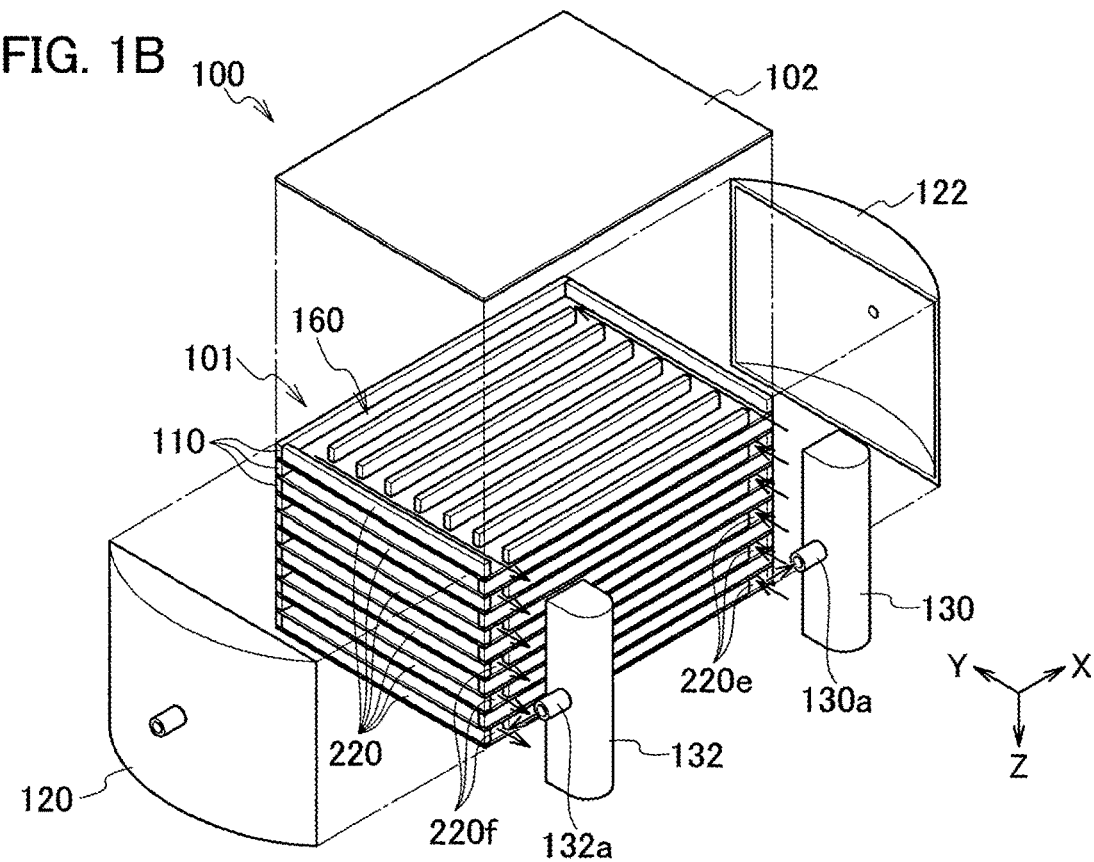
FIG. 1B is a view showing a structure of a reactor according to an embodiment of the present disclosure and illustrating a flow of a heat medium.

FIGS. 1A and 1B are exploded perspective views showing a structure of a reactor 100 according to an embodiment of the present disclosure. FIG. 1A is a view illustrating a flow of a reaction fluid, and FIG. 1B is a view illustrating a flow of a heat medium. The reactor 100 is of a heat exchanger-type, and includes a heat exchange body 101, a reaction fluid introduction part 120 and a product drain part 122, and a heat medium introduction part 130 and a heat medium drain part 132. FIG. 1A does not indicate structured catalysts described below for brevity.

The heat exchange body 101 has a counter flow-type structure in which a reaction fluid flows in a direction opposite to a flowing direction of a heat medium, and includes a plurality of first heat transfer bodies 210 and second heat transfer bodies 220, and a lid body 102. The heat exchange body 101 is supported by thermal insulating pillars (not shown). The first heat transfer bodies 210, the second heat transfer bodies 220, and the lid body 102 are each a rectangular plate-like member made of a heat transfer material having thermal resistance. The respective first heat transfer bodies 210 include a plurality of grooves composing reaction channels, more particularly, branch channels. The respective second heat transfer bodies 220 include a plurality of grooves composing heat medium channels, more particularly, branch channels and merging channels. The first heat transfer bodies 210 and the second heat transfer bodies 220 are stacked alternately in the vertical direction with the flat plate surfaces parallel to the horizontal plane, and the lid body 102 is placed on the uppermost side of the alternately-stacked heat transfer bodies in the vertical direction, so as to form the heat exchange body 101 as a stacked body. When the heat exchange body 101 is assembled, the respective members are fixed to each other by a bonding method such as tungsten inert gas (TIG) welding or diffusion bonding, so as to suppress a reduction in heat transfer derived from poor contact between the respective members.

Figure 2A:
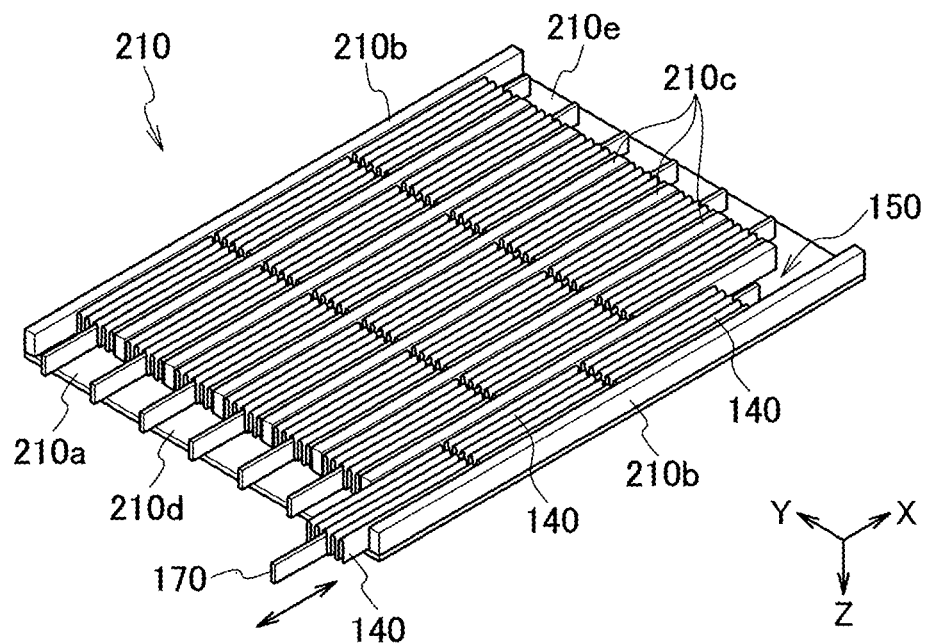
FIG. 2A is a view showing a structure of a first heat transfer body.
Figure 2B:
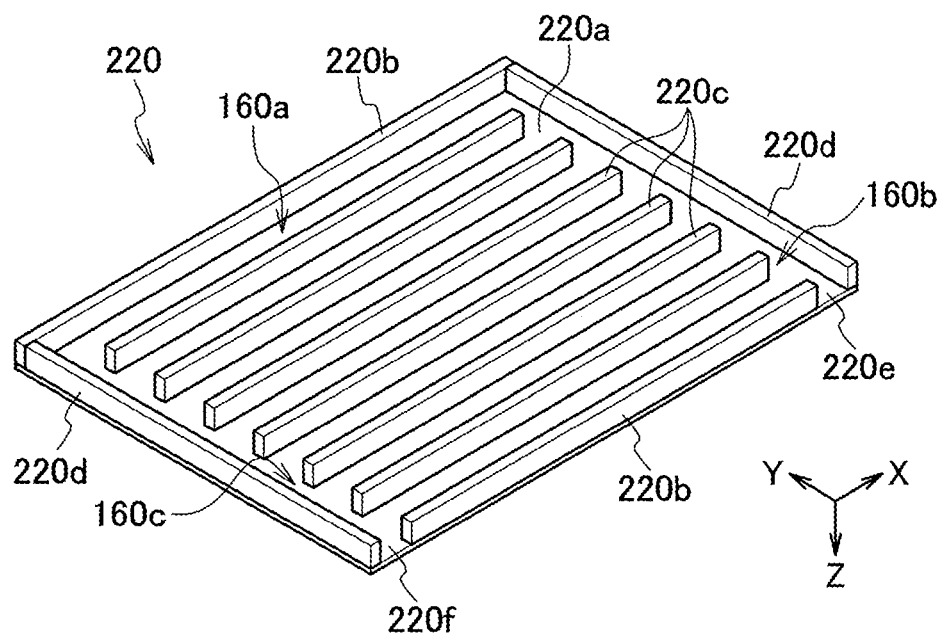
FIG. 2B is a view showing a structure of a second heat transfer body.

FIGS. 2A and 2B are perspective views showing a structure of each of the first heat transfer body 210 and the second heat transfer body 220. FIG. 2A is a view illustrating the structure of the first heat transfer body 210, and FIG. 2B is a view illustrating the structure of the second heat transfer body 220. Hereinafter, the branch channels branched in the reaction channels are simply referred to as "the reaction channels 150", instead of "the branch channels of the reaction channels", for brevity and illustration purposes.

The first heat transfer bodies 210 receive heat or cold supplied from the heat medium or the second heat transfer bodies 220 to supply the received heat or cold to the reaction fluid. The first heat transfer bodies 210 each include a base 210a, two side walls 210b, and at least one interposition wall 210c. The present embodiment illustrates six interposition walls 210c. The base 210a is a plate-like part defining the bottom surface of the reaction channels 150. The side walls 210b are extending plate-like parts extending upward and elongated in the X-axis direction at ends in the Y-axis direction on the base 210a. The interposition walls 210c are extending plate-like parts extending upward on the base 210a and arranged in parallel to the side walls 210b. The side walls 210b and the interposition walls 210c define the side surfaces of the respective reaction channels 150. The plural grooves serving as the reaction channels 150 are thus provided between the respective walls on the base 210a. When the second heat transfer boy 220 is stacked on the first heat transfer body 210, the lower surface of the second heat transfer body 220 defines the upper surface of the reaction channels 150. The first heat transfer body 210 is thus provided with the plural reaction channels 150 having a rectangular shape in cross section in the direction perpendicular to the X-axis direction, in which openings serving as reaction fluid introduction inlets 210d from which the reaction fluid is introduced are open on one side in the X-axis direction, and openings serving as product drain outlets 210e from which the product is drained are open on the other side in the X-axis direction. This structure causes the reaction fluid to flow straight through the reaction channels 150 from the reaction fluid introduction inlets 210d toward the product drain outlets 210e, as indicated by the arrows in FIG. 1A. When a plurality of reaction channels 150 are provided as described in the present embodiment, the plural interposition walls 210c are preferably arranged in parallel at regular intervals between the two side walls 210b.

The respective reaction channels 150 are provided with structured catalysts 140 held by holding members 170 as shown in FIG. 2A, which will be described below.

The second heat transfer bodies 220 supply heat or cold supplied from the heat medium directly and indirectly to the reaction fluid via the first heat transfer bodies 210. The second heat transfer bodies 220 each include a base 220a, two side walls 220b, at least one interposition wall 220c, and two end walls 220d. The base 220a is a plate-like part defining the bottom surface of heat medium channels 160. The side walls 220b are extending plate-like parts extending upward and elongated in the X-axis direction at ends in the Y-axis direction on the base 220a. The interposition wall 220c is an extending plate-like part extending upward on the base 220a and arranged in parallel to the side walls 220b. The present embodiment illustrates six interposition walls 220c. The end walls 220d are extending plate-like parts elongated in the Y-axis direction and extending upward at ends in the X-axis direction on the base 220a. The side walls 220b, the interposition walls 220c, and the end walls 220d define the side surfaces of a plurality of branch channels 160a of the heat medium channels 160. The plural grooves serving as the heat medium channels 160 are thus provided between the respective walls on the base 220a. When the first heat transfer body 210 or the lid body 102 is stacked on the second heat transfer body 220, the lower surface of the first heat transfer body 210 or the lid body 102 defines the upper surface of the heat medium channels 160, as in the case of the first heat transfer body 210. The second heat transfer body 220 has a structure in which the two side walls 220*b* having different lengths in the X-axis direction and the two end walls 220*d* define two openings on one side in the Y-axis direction, the two openings including a heat medium introduction inlet 220*e* from which the heat medium is introduced on one side in the X-axis direction, and a heat medium drain outlet 220*f* from which the heat medium is drained on the other side in the X-axis direction. The heat medium channels 160 thus include a first merging channel 160*b* extending from the heat medium introduction inlet 220*e* in the Y-axis direction and having a rectangular shape in cross section in the direction perpendicular to the X-axis direction, a plurality of branch channels 160*a* extending in the X-axis direction and each communicating with the first merging channel 160*b*, and a second merging channel 160*c* extending toward the heat medium drain outlet 220*f* in the Y-axis direction and communicating with the respective branch channels 160*a*. In this structure, the heat medium entering the heat medium channels 160 from the heat medium introduction inlet 220*e* flows through the plural branch channels 160*a* and is then drained outward from the heat medium drain outlet 220*f*, as indicated by the arrows in FIG. 1B. When a plurality of reaction channels 150 are provided in the first heat transfer body 210 as described in the present embodiment, the plural interposition walls 220*c* in the second heat transfer body 220 are also preferably arranged in parallel at regular intervals between the two side walls 220*b* so as to correspond to the arrangement of the plural reaction channels 150.

The heat transfer material used for the respective elements included in the heat exchange body 101 is preferably heat-resistant metal such as an iron alloy or a nickel alloy. More particularly, the heat-resistant alloy may be an iron alloy such as stainless steel, or a nickel alloy such as Inconel alloy 625 (registered trademark), Inconel alloy 617 (registered trademark), and Haynes alloy 230 (registered trademark). These heat transfer materials are preferable because such alloys have durability or corrosion resistance with respect to a promotion of the reaction in the reaction channels or combustion gas which may be used as a heat medium. However, the present disclosure is not intended to be limited to these materials. Alternatively, the heat transfer material may be iron-based plated steel, metal covered with heat-resistant resin such as fluororesin, or carbon graphite.

Although the heat exchange body 101 may be composed of a single first heat transfer body 210 and a single second heat transfer body 220, a larger number of the first heat transfer bodies 210 and the second heat transfer bodies 220 can improve the heat exchange performance. The heat exchange body 101 according to the present embodiment thus includes a plurality of first heat transfer bodies 210 and a plurality of second heat transfer bodies 220. The number of the second heat transfer bodies 220 is set to be larger by one than the number of the first heat transfer bodies 210. The second heat transfer bodies 220 are positioned at the uppermost end and the lowermost end on both sides of the heat exchange body 101 in the vertical direction, so that all of the first heat transfer bodies 210 are held between the second heat transfer bodies 220. The heat exchange body 101 is preferably covered with a housing or a heat insulating material so as to suppress thermal radiation from the heat exchange body 101 to prevent heat loss. The reactor 100 may include a plurality of heat exchange bodies 101 covered with a single housing.

The present embodiment illustrates the case in which seven reaction channels 150 are provided in each first heat transfer body 210, and seven branch channels 160*a* are provided in each second heat transfer body 220 to be opposed to the respective reaction channels 150 in the vertical direction. The number of the respective channels is not limited to seven, and may be determined as appropriate in view of the conditions for designing the heat exchange body 101 and the heat transfer efficiency of the heat exchange body 101. The present embodiment also illustrates the case in which the grooves composing the reaction channels 150 and the heat medium channels 160 are formed in the first heat transfer bodies 210 and the second heat transfer bodies 220 only on one side in the vertical direction. Alternatively, the grooves may be formed in the respective first heat transfer bodies 210 and second heat transfer bodies 220 on both sides in the vertical direction, so as to provide the reaction channels 150 and the heat medium channels 160 as vertically-collective grooves in the stacked state.

The reaction fluid introduction part 120 is made of a panel curved into a concave shape covering the side surface of the heat exchange body 101 at which the reaction fluid introduction inlets 210*d* are located while providing a predetermined space between the heat exchange body 101 and the reaction fluid introduction part 120. The reaction fluid introduction part 120 is detachable or openable with respect to the heat exchange body 101. The reaction fluid introduction part 120 includes an introduction inlet 120*a* from which the reaction fluid is externally introduced to the inside of the heat exchange body 101. The product drain part 122 is made of a panel curved into a concave shape covering the side surface of the heat exchange body 101 at which the product drain outlets 210*e* are located while providing a predetermined space between the heat exchange body 101 and the product drain part 122. The product drain part 122 is detachable or openable with respect to the heat exchange body 101. The product drain part 122 includes a drain outlet 122*a* from which the product is drained outward from the inside of the heat exchange body 101.

The heat medium introduction part 130 is a vertically-elongated hollow member. The heat medium introduction part 130 includes an opening (not shown) covering the heat medium introduction inlets 220*e* in the heat exchange body 101, and an introduction inlet 130*a* from which the heat medium is externally introduced to the inside of the heat exchange body 101. The heat medium drain part 132 is a vertically-elongated hollow member similar to the heat medium introduction part 130. The heat medium drain part 132 includes an opening (not shown) covering the plural heat medium drain outlets 220*f* in the heat exchange body 101, and a drain outlet 132*a* from which the heat medium is drained outward from the inside of the heat exchange body 101.

The introduction inlet 120*a* and the drain outlet 122*a* of the reaction fluid introduction part 120 and the product drain part 122 are preferably located in the middle in the space facing the heat exchange body 101, in particular, in the middle on the Y-Z plane, as shown in FIGS. 1A and 1B. The reason for this is to distribute the well-balanced amount of the reaction fluid introduced from the introduction inlet 120*a* to the respective reaction channels 150 and drain the reaction fluid from the drain outlet 122*a* efficiently. The introduction inlet 130*a* and the drain outlet 132*a* of the heat medium introduction part 130 and the heat medium drain part 132 are also preferably located in the middle in the space facing the heat exchange body 101, in particular, at the intermediate position in the vertical direction, as shown in FIGS. 1A and 1B. The reason for this is to distribute the well-balanced amount of the heat medium introduced from the introduction inlet 130a to the respective heat medium channels 160 and drain the heat medium from the drain outlet 132a efficiently.

The heat exchange body 101 may be any of a liquid-liquid heat exchanger, a gas-gas heat exchanger, and a gas-liquid heat exchanger, and the reaction fluid and the heat medium supplied to the reactor 100 may be either gas or liquid. The reactor 100 can be applied to a compact reactor, which has a large specific surface area per unit mass in the reaction channels, so as to cause chemical synthesis through various kinds of thermal reactions such as an endothermic reaction and an exothermic reaction. Examples of such thermal reactions causing synthesis include: a steam reforming reaction of methane as represented by the following chemical equation (1); an endothermic reaction such as a dry reforming reaction of methane as represented by the following chemical equation (2); a shift reaction as represented by the following chemical equation (3); a methanation reaction as represented by the following chemical equation (4); and a Fischer-Tropsch synthesis reaction as represented by the following chemical equation (5). The reaction fluid used in these reactions is in a gas state.

$$CH_4 + H_2O \rightarrow 3H_2 + CO \qquad (1)$$

$$CH_4 + CO_2 \rightarrow 2H_2 + 2CO \qquad (2)$$

$$CO + H_2O \rightarrow CO_2 + H_2 \qquad (3)$$

$$CO + 3H_2 \rightarrow CH_4 + H_2O \qquad (4)$$

$$(2n+1)H_2 + nCO \rightarrow CnH_{2n+2} + nH_2O \qquad (5)$$

The reactor 100 may also be used for causing other reactions not described above, such as an acetylation reaction, an addition reaction, an alkylation reaction, a dealkylation reaction, a hydrodealkylation reaction, a reductive alkylation reaction, an amination reaction, an aromatization reaction, an acylation reaction, a self-heating reforming reaction, a carbonylation reaction, a decarbonylation reaction, a reductive carbonylation reaction, a carboxylation reaction, a reductive carboxylation reaction, a reductive coupling reaction, a condensation reaction, a cracking reaction, a hydrocracking reaction, a cyclization reaction, a cyclooligomerization reaction, a dehalogenation reaction, a dimerization reaction, an epoxidation reaction, an esterification reaction, an exchange reaction, a halogenation reaction, a hydrogenation reaction, a hydrohalogenation reaction, a homologation reaction, a hydration reaction, a dehydration reaction, a hydrogenation reaction, a dehydrogenation reaction, a hydrocarboxylation reaction, a hydroformylation reaction, a hydrogenolysis reaction, a hydrometalation reaction, a hydrosilylation reaction, a hydrolyzation reaction, a hydroprocessing reaction, an isomerization reaction, a methylation reaction, a demethylation reaction, a metathesis reaction, a nitration reaction, an oxidation reaction, a partial oxidation reaction, a polymerization reaction, a reduction reaction, a reverse water gas shift reaction, a sulfonation reaction, a telomerization reaction, a transesterification reaction, and a trimerization reaction.

The reactor 100 uses, as the reaction fluid, a fluid including a substance such as a raw material involved in the chemical reaction as described above as a reactant. The reaction fluid flowing through the reaction channels 150 receives heat or cold of the heat medium passing through the heat medium channels 160, and is heated or cooled to promote the reaction, so that the reactant is converted into a target product. The reaction fluid may contain a carrier not involved in the reaction. Such a carrier may be selected as appropriate from substances not influencing the promotion of the reaction in view of the chemical reaction to be induced. The carrier usable for the reaction fluid particularly in a gas state may be a gas carrier of inert gas or a gaseous substance with low reactivity. The heat medium is preferably a fluid substance not corroding the constituent materials of the reactor 100, and may be a liquid substance such as water or oil, or a gaseous substance such as combustion gas. The gaseous substance used as the heat medium is easier to handle than the liquid medium.

As shown in FIG. 2A, the structured catalysts 140 are installed in the respective reaction channels 150 so as to promote the reaction of the reactant. A catalyst included in the structured catalysts 140 is selected as appropriate from substances which mainly contain active metal effective in the progress of the chemical reaction as described above and are suitable for the promotion of the reaction based on the synthesis reaction executed in the reactor 100. Examples of active metal as a catalytic component include nickel (Ni), cobalt (Co), iron (Fe), platinum (Pt), nithenium (Ru), rhodium (Rh), and palladium (Pd). These metals may be used singly, or may be used in combination as long as the combination is effective in the promotion of the reaction. The structured catalysts 140 are prepared such that the catalyst is supported on a structure material, for example. The structure material is selected as appropriate from heat-resistant metals which can be molded and support the catalyst. A structure, serving as the structured catalysts 140, may have a corrugated plate-like shape having a wave-like form in cross section or a jaggedly corrugated shape, so as to increase the contact area with the reaction fluid. Examples of such heat-resistant metals include iron (Fe), chromium (Cr), aluminum (Al), yttrium (Y), cobalt (Co), nickel (Ni), magnesium (Mg), titanium (Ti), molybdenum (Mo), tungsten (W), niobium (Nb), tantalum (Ta), and a heat-resistant alloy mainly containing some of these metals. The structured catalysts 140 may be obtained such that a thin plate structure material made of a heat-resistant alloy such as Fecralloy (registered trademark) is molded. Examples of methods of supporting the catalyst include a method of directly supporting the catalyst on the structure material by surface modification or the like, and a method of indirectly supporting the catalyst on the structure material via a carrier. Practically, the use of the carrier facilitates the process of supporting the catalyst. The carrier is selected as appropriate from materials having durability without impeding the promotion of the reaction and capable of supporting the catalyst satisfactorily in view of the reaction executed in the reactor 100. The carrier may be a metal oxide such as alumina ($Al_2O_3$), titanic ($TiO_2$), zirconia ($ZrO_2$), ceria ($CeO_2$), or silica ($SiO_2$). These metal oxides may be used singly, or some of these metal oxides may be selected and combined together. The supporting method by use of the carrier may include a process of forming a mixed layer of the catalyst and the carrier on the surface of the structure material molded, or a process of forming a support layer and then supporting the catalyst on the support layer by surface modification or the like.

A single structured catalyst 140, or a plurality of structured catalysts 140 arranged in series as shown in FIG. 2A, may be installed in each reaction channel 150. The state in which the plural structured catalysts 140 are arranged in series may be applied to the following case. First, the structured catalyst 140 can only have a limited length for reasons of manufacture. When the length of the reaction channels is set to be relatively long in order to improve the reaction efficiency in the heat exchange body 101, a single structured catalyst 140 is not sufficient to entirely or efficiently fill the inside of each reaction channel 150 in the length direction. Thus, the plural structured catalysts 140 are preferably aligned in each reaction channel 150. In addition, when the amount of the reactant introduced in the reaction channels 150 is relatively large, carbon coking may be caused on the surface of the structured catalysts 140, which tends to lead to a decrease in activity or deterioration of the catalyst. Further, when dust is mixed in the reaction fluid, a reaction channel 150 may be blocked by the dust to result in a decrease in reaction efficiency. In order to deal with these problems, a plurality of structured catalysts 140, or a single structured catalyst divided into plural parts, is arranged in series and installed in each reaction channel 150, so that only a part of the structured catalysts 140 deteriorated or blocked can be replaced without all of the structured catalysts 140 changed. Accordingly, the amount of the structured catalysts 140 to be replaced can be minimized, so as to reduce costs necessary for performance adjustment or maintenance of the reactor 100.

Figure 3A:
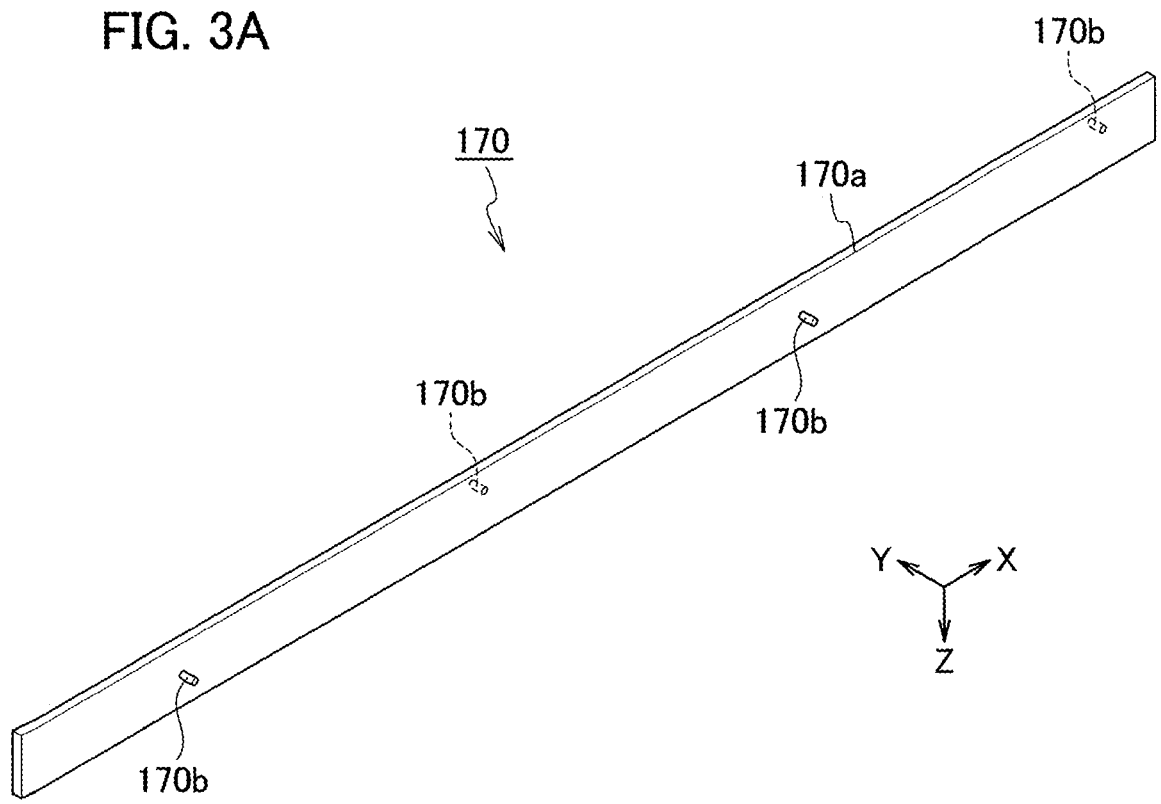
FIG. 3A is a view showing a structure of a holding member according to a first embodiment.
Figure 3B:
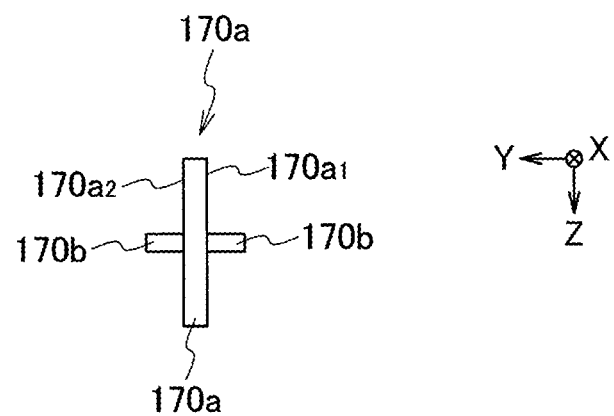
FIG. 3B is a side view showing a structure of a holding member according to a first embodiment.
Figure 4A:
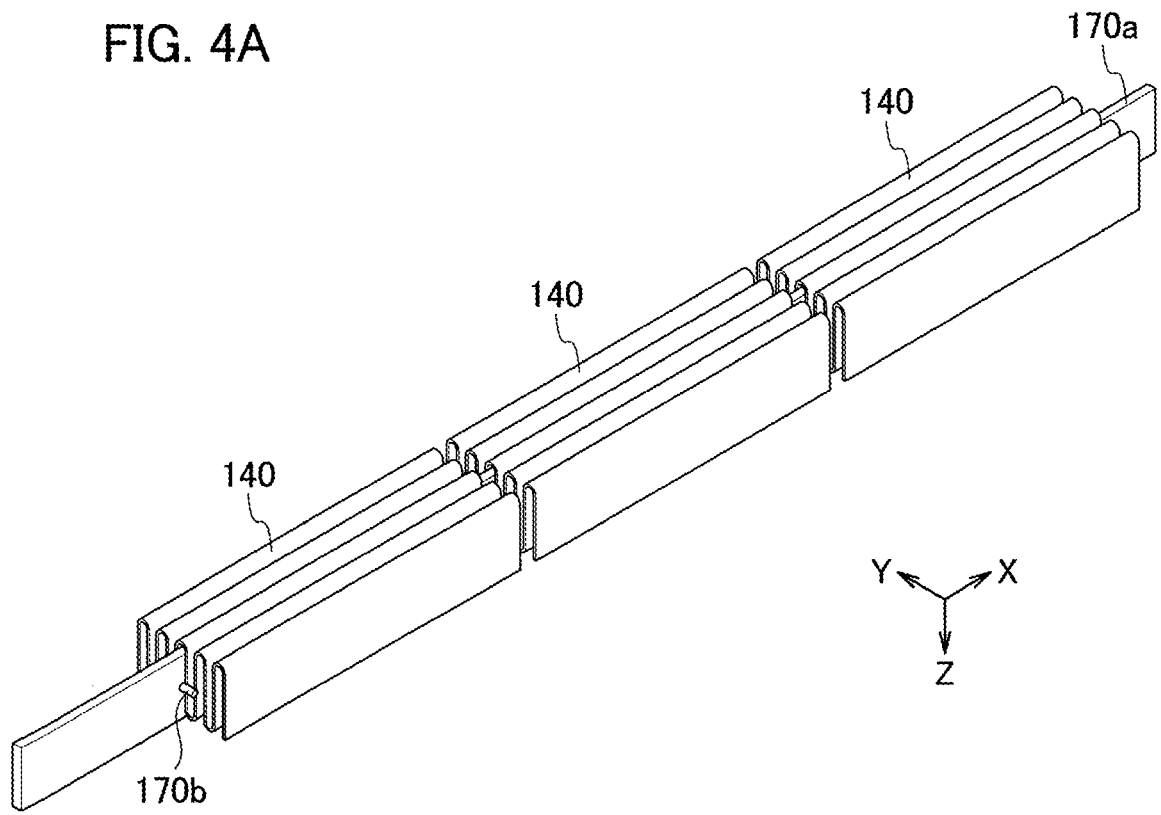
FIG. 4A is a view illustrating a state of holding structured catalysts according to the first embodiment.
Figure 4B:
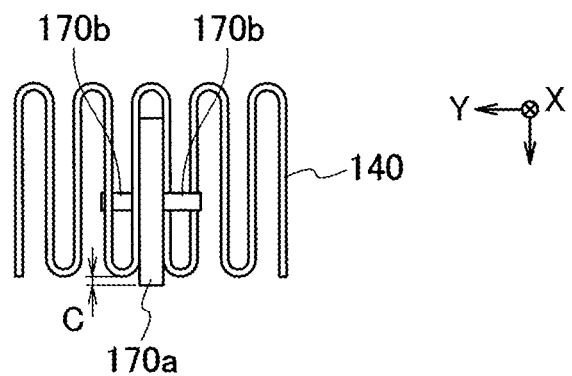
FIG. 4B is a view illustrating a state of holding structured catalysts according to the first embodiment.

As shown in FIG. 2A, the reactor 100 includes a plurality of holding members 170. The holding members 170 each can integrally hold the plural structured catalysts 140 in each reaction channel 150. The present embodiment illustrates the case in which each holding member 170 holds three structured catalysts 140. FIGS. 3A and 3B are views showing a structure of the holding member 170. FIGS. 4A and 4B are views illustrating a state in which the holding member 170 holds the plural structured catalysts 140. Each holding member 170 includes an extending part 170a and projections 170b provided on the extending part 170a. As shown in FIG. 4A, the structured catalysts 140 each extend in the X-axis direction and have a corrugated plate-like shape having a wave-like form in cross section, for example.

The extending part 170a is a body of the holding member 170 extending and conforming to the shape of the reaction channel 150 in the extending direction and engaging at least partly with the respective structured catalysts 140. The extending part 170a has a plate-like shape. For example, the extending part 170a may be a plate-like member having a first side surface $170a_1$ and a second side surface $170a_2$ which are two main surfaces opposed to each other on the front and rear sides and brought into contact with opposed two surfaces composing part of the wave-like form of each structured catalyst 140. The respective structured catalysts 140 having a wave-like form in cross section partly engage with the extending part 170a to interpose the extending part 170a therebetween. The structured catalysts 140 are thus hung on the extending part 170a so as not to drop off in the vertical direction. In addition, the structured catalysts 140 are prevented from shifting in the extending direction owing to frictional force due to the contact with the extending part 170a, and are prevented from shifting in the lateral direction since the respective structured catalysts 140 interpose the extending part 170a.

The extending part 170a preferably has a cross-sectional shape such that the structured catalysts 140 are not brought into contact with the inner wall of the reaction channel 150 when the holding member 170 engaging with the structured catalysts 140 is placed in the reaction channel 150. For example, the extending part 170a preferably has a cross section partly projecting outward from the outermost part of the structured catalysts 140 in the state in which the extending part 170a engages with the structured catalysts 140. FIG. 4B illustrates a case in which the extending part 170a projects from the outermost part of the structured catalysts 140 in the vertical direction by the difference C in height. Therefore, only the extending part 170a is brought into contact with the inner wall of the reaction channel 150 in the vertical direction, which is on the lower surface side in FIG. 4B, when the holding member 170 engaging with the structured catalysts 140 is placed in the reaction channel 150. In addition, the extending part 170a preferably has a cross-sectional shape such that the structured catalysts 140 are not brought into contact with the inner wall of the reaction channel 150 on the minus side in the vertical direction, which is the upper surface side in FIG. 4B, when the holding member 170 is placed in the reaction channel 150. The extending part 170a having the cross-sectional shape as described above can increase the contact area of the structured catalysts 140 with the reaction fluid so as to use the structured catalysts 140 effectively.

The projections 170b are regulating parts for regulating the movement of the structured catalysts 140 in the extending direction of the extending part 170a. The projections 170b are arranged at intervals each conforming to the length of the structured catalysts 140 in the extending direction of the extending part 170a, and project on the first side surface $170a_1$ or the second side surface $170a_2$ in the direction crossing the extending direction of the extending part 170a, for example. The projecting height of the projections 170b has a length such that part of the structured catalysts 140 overlaps with part of the projections 170b in the extending direction in the state in which the extending part 170a engages with the structured catalysts 140, as shown in FIG. 4B. The projecting height is a length in the direction perpendicular to the extending direction in the present embodiment, but does not necessarily correspond to the length exactly in the perpendicular direction. Each structured catalyst 140 engages with the extending part 170a between a first projection 170b located at a position capable of coming into contact with one side of the structured catalyst 140 in the extending direction and a second projection 170b located at a position capable of coming into contact with the other side of the structured catalyst 140 in the extending direction. In order to accurately position, namely, arrange each structured catalyst 140 at a predetermined position in the reaction channel 150, the first projection 170b and the second projection 170b are preferably arranged such that the both projections 170b are brought into contact with the structured catalyst 140 interposed therebetween. However, a gap may be present to a certain extent between the structured catalyst 140 and the respective adjacent projections 170b when the structured catalyst 140 engages with the extending part 170a, in order to facilitate the attachment of the structured catalysts 140 to the holding member 170 or hold the structured catalysts 140 having various lengths. In addition, the projections 170b adjacent to each other in the extending direction preferably project in opposite directions from the extending part 170a, as shown in FIG. 3A. If the projections 170b all project in the same direction, a force applied when removing the holding member 170 from the reaction channel 150 may be biased toward the projecting side on the basis of the extending part 170a. The biased removing force may bend the holding member 170 to cause the structured catalysts 140 to be stuck on the interposition walls 210c or the like defining the reaction channel 150. Such a state prevents the structured catalysts 140 from being removed easily. The adjacent projections 170b projecting in the opposite directions according to the present embodiment can suppress such a biased removing force. The projections 170b may be obtained such that the extending part 170a is partly notched and bent, or the projections 170b preliminarily formed into a pin-like shape may be fixed to the extending part 170a by welding.

The material used for the extending part 170a and the projections 170b is preferably selected from metals having high thermal resistance and high durability with less influence on the reaction processing in the reaction channels 150, as in the case of the structure composing the structured catalysts 140 described above.

Figure 5A:
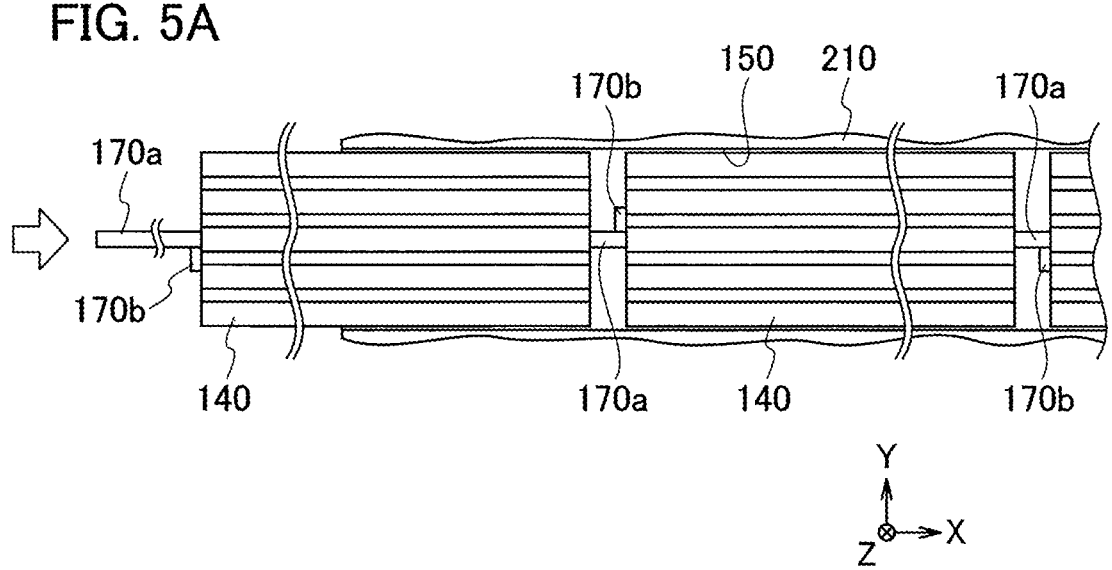
FIG. 5A is a view illustrating a state in which the structured catalysts are inserted in the reaction channel according to the first embodiment.
Figure 5B:
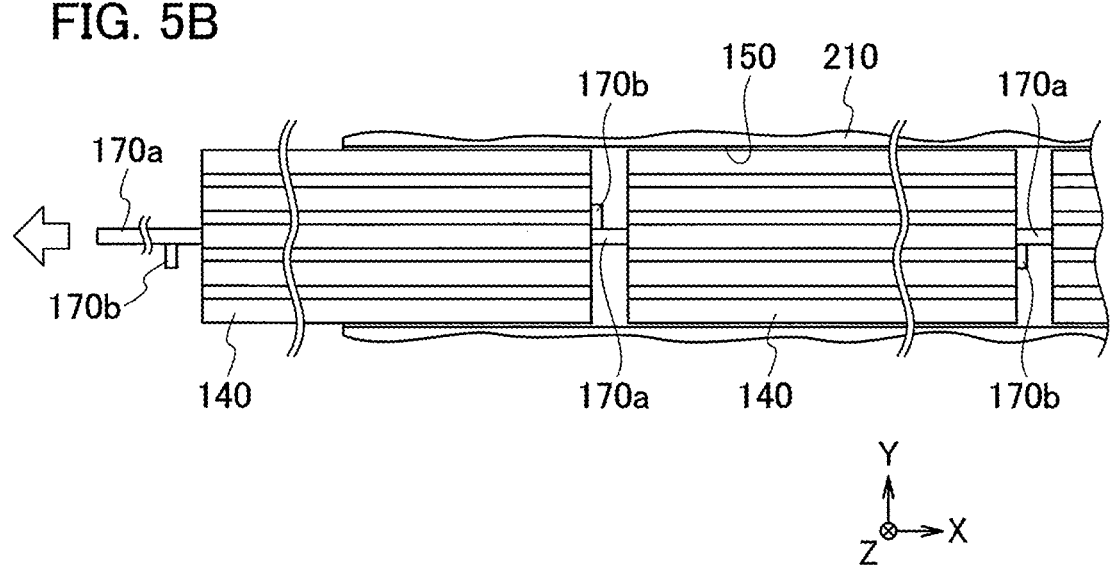
FIG. 5B is a view illustrating a state in which the structured catalysts are removed from the reaction channel according to the first embodiment.

FIGS. 5A and 5B are plan views showing the holding member 170 and the structured catalysts 140 when the structured catalysts 140 are installed in or removed from the reaction channel 150. FIG. 5A is a view illustrating a state in which the structured catalysts 140 are inserted in the reaction channel 150, and FIG. 5B is a view illustrating a state in which the structured catalysts 140 are removed from the reaction channel 150. As described above, the interval between the respective adjacent projections 170b is preferably set to correspond to the length of the structured catalyst 140 so that the adjacent projections 170b are both in contact with the structured catalyst 140 engaging with the extending part 170a. FIGS. 5A and 5B illustrate, however, the case in which there is a gap between the structured catalyst 140 and at least one of the adjacent projections 170b.

Before the reactor 100 starts the reaction processing, the operator opens the reaction fluid introduction part 120 to install the structured catalysts 140 suitable for the reaction promotion in the respective reaction channels 150. In particular, according to the present embodiment, the operator inserts the holding member 170 preliminarily holding the plural structured catalysts 140 into the reaction channel 150 in the direction as indicated by the arrow in FIG. 5A. Since the plural structured catalysts 140 are integrally held by the holding member 170, the operator can install the plural structured catalysts 140 simultaneously by inserting one holding member 170 into each reaction channel 150 while holding one end of the holding member 170. In addition, since the respective structured catalysts 140 are held by the holding member 170 with certain accuracy in positioning on the basis of the projections 170b before the insertion, the operator temporarily inserts the structured catalysts 140 and then moves the end of the holding member 170 as necessary, so as to easily place the structured catalysts 140 at predetermined positions. The amount of displacement of the structured catalysts 140 along the holding member 170 during the insertion is at most within the gap between each structured catalyst 140 and the adjacent projections 170b. The projections 170b keep pushing the structured catalysts 140 toward the plus side in the X-axis direction. Therefore, as the difference between the interval between the adjacent projections 170b and the length of each structured catalyst 140 interposed therebetween is small, the influence on the final positioning of the structured catalysts 140 in the reaction channel 150 can be decreased. In contrast, it takes much time to install the structured catalysts in the conventional reactor, typically including a large number of reaction channels, since the operator needs to position and insert the plural structured catalysts one by one so as to install the structured catalysts in series at preferred positions in the reaction channel.

When the reaction processing in the reactor 100 ends, the operator opens the reaction fluid introduction part 120 again to remove the structured catalysts 140 from the reaction channel 150 when the structured catalysts 140 need to be replaced, for example. In particular, according to the present embodiment, since the plural structured catalysts 140 are integrally held by the holding member 170, the operator holds the one end of the holding member 170 and moves it in the direction as indicated by the arrow in FIG. 5B, so as to easily remove all of the structured catalysts 140 from the reaction channel 150. In addition, since the arrangement of the structured catalysts 140 is kept, the operator can temporarility remove the holding member 170, replace a target structured catalyst 140 located at a particular position, and then place the holding member 170 back to the reaction channel 150 easily. In the conventional reactor, it is difficult to remove the structured catalyst 140 located on the backmost side in the reaction channel 150 when the installation or removal of the structured catalysts 140 is possible only either from the upstream side or the downstream side of the reaction channel 150 for the structural reasons in the reactor. According to the present embodiment, the easiness of removal is not dependent on which side the structured catalyst 140 is removed from. In addition, the projections 170b keep pushing the structured catalysts 140 toward the minus side in the X-axis direction while being in contact with the structured catalysts 140, as shown in FIG. 5B, even when the structured catalysts 140 are displaced along the holding member 170 during the removal. Therefore, the holding member 170 prevents any structured catalyst 140 from remaining in the reaction channel 150 during the removal. Further, since the respective projections 170b apply the removing force evenly to the respective structured catalysts 140, there is no risk of concentrating the removing force on a particular structured catalyst 140 to damage the structured catalyst 140. In contrast, it takes much time to remove the plural structured catalysts 140 particularly arranged in series in one reaction channel, since the operator needs to remove the structured catalysts one by one from the reaction channel.

The holding member 170 remains installed in the reaction channel 150 during the reaction processing in the reactor 100 in the state in which the plural structured catalysts 140 are integrally aligned in one reaction channel 150 via the holding member 170. In the conventional reactor, a frictional force caused by the contact with the respective walls of the reaction channel is only applied to each structured catalyst. According to the present embodiment, the reactor 100 hardly causes the displacement of the structured catalysts 140 when the flowing pressure of the fluid during the reaction processing is applied to the structured catalysts 140, as compared with the conventional reactor, since not only a frictional force caused by the contact with the extending part 170a but also a frictional force caused by the contact between the extending part 170a and the respective walls of the reaction channel 150 are applied to each structured catalyst 140.

As described above, the present embodiment can provide the reactor having a structure capable of facilitating the installation and removal of the structured catalysts with respect to the reaction channels and ensuring the positional stability of the structured catalysts in the reaction channels.

Second Embodiment

A reactor according to a second embodiment of the present disclosure is described below. While the fundamental structure of the reactor according to the present embodiment is substantially the same as that in the first embodiment, the reactor according to the present embodiment further includes a positioning mechanism for positioning the structured catalysts 140 in the reaction channels 150.

Figure 6:
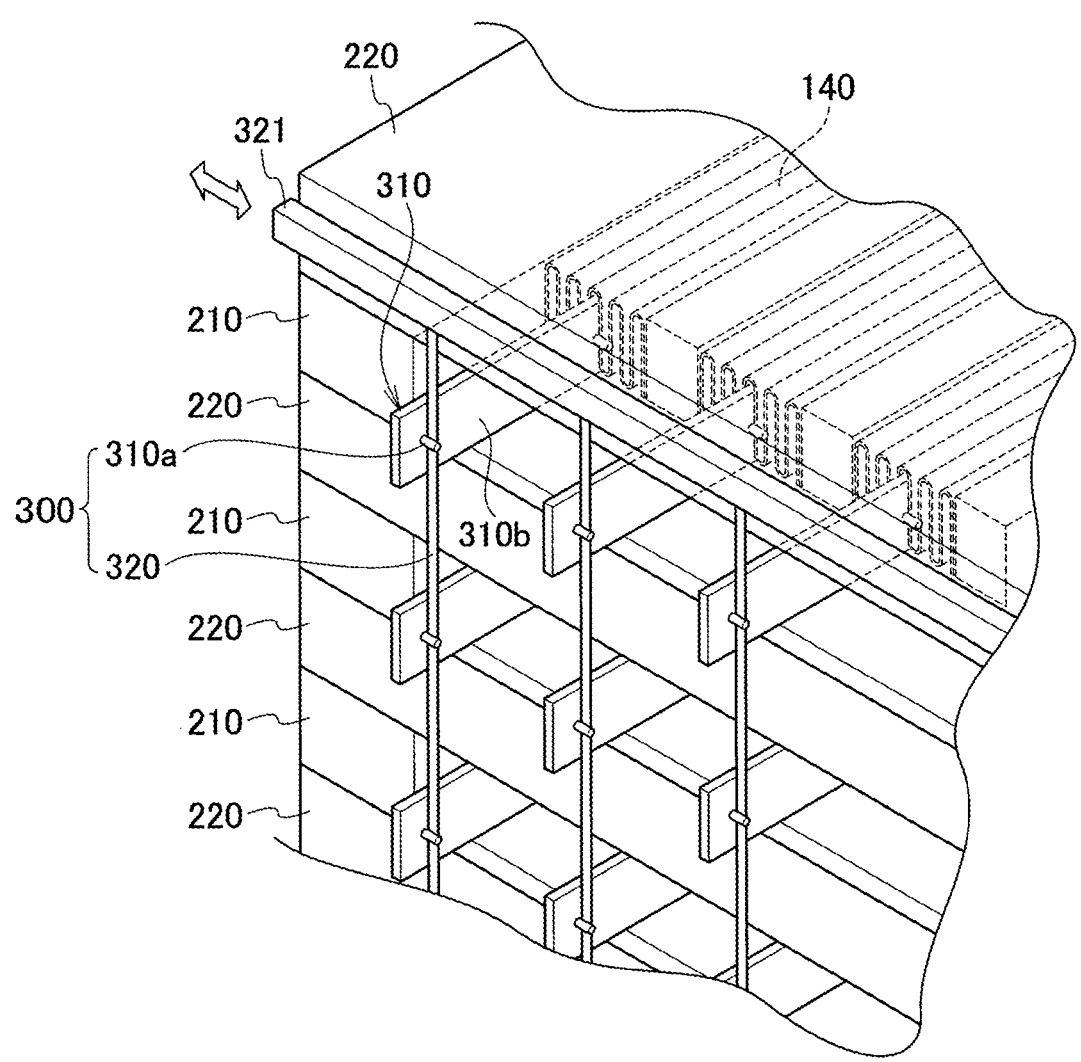
FIG. 6 is a view showing a structure of a positioning mechanism according to a second embodiment.

FIG. 6 is a perspective view partly showing a structure of a positioning mechanism 300 according to the present embodiment. The positioning mechanism 300 includes an engaging part 310*a* provided at least at one end of an extending part 310*b* in the extending direction, and a reference member 320 in contact with the engaging part 310*a* in a state in which a holding member 310 is installed in the reaction channel 150.

The fundamental structure of the holding member 310 is substantially the same as the holding member 170 in the first embodiment. However, the holding member 310 is characterized in that at least one end of the extending part 310*b* in the extending direction projects to the outside of the heat exchange body 101 in the state in which the respective structured catalysts 140 are placed at substantially predetermined positions in the reaction channel 150. In particular, the extending part 310*b* on the reaction fluid introduction side of the reaction channel 150 projects toward the minus side in the X-axis direction, as shown in FIG. 6, as in the case of the first embodiment. The engaging part 310*a* is located at the projecting part of the extending part 310*b*. The engaging part 310*a* may have substantially the same shape as the plural projections 170*b* illustrated in the first embodiment provided at other positions in the extending part 310*b*.

The reference member 320 is brought into contact with the engaging part 310*a* when the holding member 310 is inserted into the reaction channel 150 so as to prevent the further insertion of the holding member 310. The position of the engaging part 310*a* provided on the extending part 310*b* or the position of the reference member 320 is determined such that the reference member 320 is brought into contact with the engaging part 310*a* when the respective structured catalysts 140 reach the predetermined positions upon the insertion of the holding member 310. The reference member 320 is supported by a member on the heat exchange body 101 side directly or indirectly at a position not impeding the installation or removal of the holding member 310 with respect to the reaction channel 150. As used herein, the member on the heat exchange body 101 side refers to the heat exchange body 101 itself or a member holding the heat exchange body 101, for example. When the engaging part 310*a* has a pin-like shape which is the same as the projections 170*b*, the reference member 320 may have a stick-like shape extending in the vertical direction so as to come into contact with the engaging part 310*a* in the X-axis direction perpendicular to the Y-axis direction in which the engaging part 310*a* projects. The reference member 320 having a stick-like shape hardly blocks the flow of the reaction fluid when the reference member 320 is located in the flowing space of the reaction fluid. When the positioning mechanism 300 is installed on the reaction fluid introduction side of the heat exchange body 101 as described in the present embodiment, the reference member 320 is arranged so as to be brought into contact with the engaging part 310*a* on the minus side in the X-axis direction. Since the reaction fluid flows in the reaction channels 150 toward the plus side in the X-axis direction, the displacement of the reference member 320 from the fixed position can be suppressed when the holding member 310 and the structured catalysts 140 receive the flowing pressure toward the plus side in the X-axis direction.

Since the heat exchange body 101 according to the present embodiment is a stacked body including the plural first heat transfer bodies 210 and second heat transfer bodies 220 in which the plural reaction channels 150 are arranged in parallel and in layers, the reaction fluid introduction inlets 210*d*, namely, the openings of the respective reaction channels 150 regularly face the same direction. Each reference member 320 therefore may be a single stick-like body opposed to the plural holding members 310 installed in the respective reaction channels 150 arranged in layers in the vertical directions and simultaneously brought into contact with at least two engaging parts 310*a*, as shown in FIG. 6. The reference member 320 thus extends in the vertical direction with both ends located on the upper side and the lower side of the heat exchange body 101.

The positioning mechanism 300 further includes a fixing member 321 integrally fixing the upper end or the lower end or the both ends of the plural reference members 320 each having a stick-like body. The fixing member 321 is supported on the heat exchange body 101 via a relocating means (not shown) capable of shifting the fixing member 321. For example, when the operator is removing the holding member 310 from the reaction channel 150 in the state in which the reference member 320 is located at the position in contact with the engaging part 310*a* as shown in FIG. 6, the reference member 320 blocks the retreat of the holding member 310. The relocating means can move the fixing member 321 in the direction different from the extending direction of the reaction channels 150, namely, in the Y-axis direction as indicated by the arrow in FIG. 6, for example. The operator thus can shift the fixing member 321 in the Y-axis direction before inserting or removing the holding member 310 so that the reference member 320 does not block the reaction channels 150, so as to easily insert or remove the holding member 310, as in the case of the first embodiment. The shifted amount of the fixing member 321 is preferably approximately half of the channel width of the reaction channels 150.

According to the present embodiment as described above, the operator can insert the holding member 310, namely, the structured catalysts 140 in the reaction channel 150 while bringing the engaging part 310*a* into contact with the reference member 320 so as to immediately complete the positioning of the structured catalysts 140 without a position-measuring process. When the plural reaction channels 150 are arranged in parallel and in layers, the positioning mechanism 300 having the structure as shown in FIG. 6 can greatly save the trouble of installing and positioning the structured catalysts 140. Further, the reference member 320 remains brought into contact with the engaging part 310*a* during the reaction processing, and therefore, contributes to ensuring the positional stability of the structured catalysts 140.

The shape of each of the engaging part 310*a* and the reference member 320 may be any shape which can achieve the effects as described above and may be changed as appropriate. For example, the engaging part 310*a* may have an L-shape which is caught by the reference member 320 or a U-shape which holds the reference member 320, so as to further increase the positional stability of the structured catalysts 140. The reference member 320 may have a shape entirely extending in the Y-axis direction as long as the shape does not block the insertion and removal of the holding member 310. The shape of the positioning mechanism 300 can also be changed as appropriate so as to be applied to not only the case in which the plural reaction channels 150 are arranged in parallel and in layers, but also a case in which the reaction channels 150 are arranged in parallel in the Y-axis direction with a single layer or a case in which a plurality of reaction channels 150 each being a single line are stacked in layers in the vertical direction.

While the present embodiment has exemplified the case in which the positioning mechanism 300 is located on the reaction fluid introduction side of the heat exchange body 101, the positioning mechanism 300 may be located on the product drain side. This arrangement is effective particularly when the holding member 310, namely, the structured catalysts 140 can be inserted and removed only from the product drain side for the structural reasons in the reactor 100. In such a case, the reference member 320 needs to be arranged to be brought into contact with the engaging part 310a on the plus side in the X-axis direction so that the holding member 310 and the structured catalysts 140 are not displaced from the predetermined installation positions when the flowing pressure toward the plus side in the X-axis direction is applied, since the reaction fluid still flows in the reaction channels 150 toward the plus side in the X-axis direction.

Figure 7A:
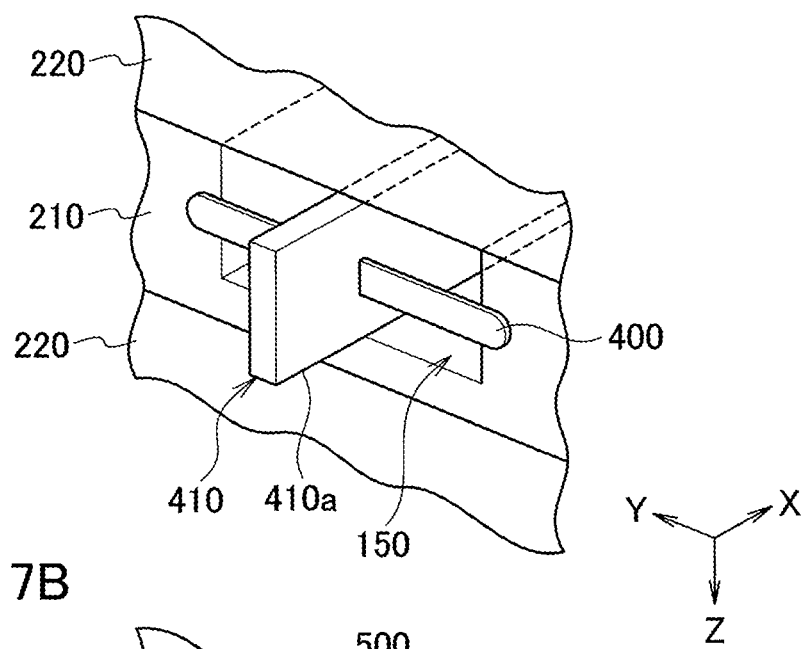
FIG. 7A is a view showing other structure of the positioning mechanism according to the second embodiment.
Figure 7B:
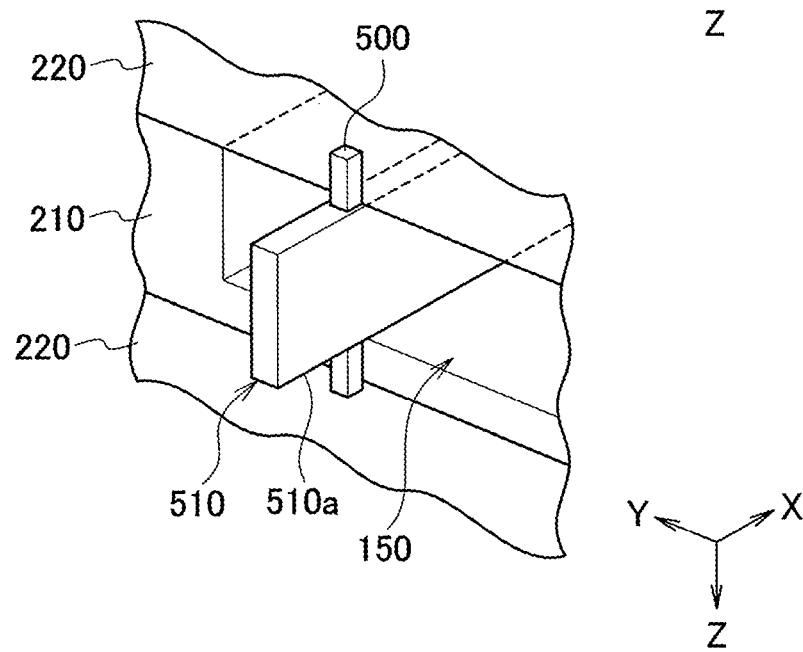
FIG. 7B is a view showing other structure of the positioning mechanism according to the second embodiment.

The structure of the positioning mechanism according to the present embodiment may further be simplified more than the structure of the positioning mechanism 300 described above. FIGS. 7A and 7B are perspective views showing other structures of the positioning mechanism according to the present embodiment.

A positioning mechanism 400 shown in FIG. 7A is a projection provided at least at one end in the extending direction of an extending part 410a composing a holding member 410. The structure of the extending part 410a is substantially the same as the extending part 310b described above. The positioning mechanism 400 is provided on the two main flat surfaces opposed to each other on the front and rear sides of the extending part 410a on which the projections 170b are provided. In particular, the positioning mechanism 400 projects on the plus side and the minus side in the Y-axis direction in FIG. 7A, so as to be brought into contact with the outer surface of the first heat transfer body 210 composing the reaction channel 150 when the holding member 410 is placed in the reaction channel 150. As shown in FIG. 7A, the positioning mechanism 400 is effective particularly when there is no step on the end surface of the first heat transfer body 210 so that the positioning mechanism 400 projecting on both plus and minus sides in the Y-axis direction is brought into contact with the outer surface of the first heat transfer body 210. The positioning mechanism 400 is not necessarily provided on the two main flat surfaces but may be provided on one of the main flat surfaces opposed to each other on the front and rear sides of the extending part 410a.

A positioning mechanism 500 shown in FIG. 7B is a projection provided at least at one end in the extending direction of an extending part 510a composing a holding member 510. The structure of the extending part 510a is also substantially the same as the extending part 310b described above. The positioning mechanism 500 differs from the positioning mechanism 400 described above in being provided on two side surfaces perpendicular to the two main flat surfaces of the extending part 510a. In particular, the positioning mechanism 500 projects on the plus side and the minus side in the Z-axis direction in FIG. 7B, so as to be brought into contact with the outer surface of the second heat transfer body 220 or the outer surface of the first heat transfer body 210 when the holding member 510 is placed in the reaction channel 150. The positioning mechanism 500 is not necessarily provided on both side surfaces of the extending part 510a but may be provided on one of the side surfaces.

The positioning mechanism 400 and the positioning mechanism 500 each may have a pin-like shape similar to the projections 170b as illustrated in the first embodiment. In order to further increase the contact area with the outer surface of the first heat transfer body 210 to improve the positional stability of the structured catalysts 140, the respective positioning mechanisms may have a plate-like shape as shown in FIG. 7A, or may be formed into a prism as shown in FIG. 7B.

Other Embodiments

The respective embodiments described above have exemplified the case in which the extending part 170a composing the holding member 170 and the like has a rectangular plate-like shape in cross section including the first side surface $170a_1$ and the second side surface $170a_2$, but the present disclosure is not limited to this case. The extending part may have various types of plate-like shapes. The extending part may have a truss structure in which a large number of holes are provided on the surfaces corresponding to the first side surface $170a_1$ and the second side surface $170a_2$, for example, as long as the structure fulfills the preferred conditions such as rigidity. The extending part having such a truss structure has the advantage of allowing the reaction fluid to come into contact with the structured catalysts 140 more easily because regions through which the reaction fluid can flow are additionally provided.

While the respective embodiments described above have exemplified the case in which the holding member 170 and the like holds a plurality of structured catalysts 140, the holding member 170 may hold a single structured catalyst 140. In such a case, the number of the projections 170b provided is at least two so as to be brought into contact with at least one of the both ends of the structured catalyst 140 when the structured catalyst 140 engages with the extending part 170a. The respective structured catalysts 140 may have different lengths because the interval between the adjacent projections 170b in the extending direction of the extending part 170a can be set to conform to the length of the corresponding structured catalyst 140.

The respective embodiments described above have exemplified the case in which the reaction channels 150 included in the heat exchange body 101 are provided such that the extending direction corresponds to the X-axis direction so as to extend straight from the reaction fluid introduction inlets 210d toward the product drain outlets 210e, but the present disclosure is not limited to this case. As described above, the holding member 170 and the like can be inserted and removed with respect to the reaction channels 150 from either the reaction fluid introduction side or the product drain side of the heat exchange body 101. For example, only one end on the reaction fluid introduction side of the respective reaction channels 150 extending straight may be open in the extending direction of the reaction channels 150 so as to provide the reaction fluid introduction inlets 210d in the same direction as the extending direction, as illustrated in the respective embodiment. In addition, the product drain side, namely, the product drain outlet of the reaction channels 150 may be open in the direction different from the extending direction of the reaction channels 150, for example, in the direction perpendicular to the extending direction of the reaction channels 150, as in the case of the heat medium drain outlet 220f communicating with the second merging channel 160c included in the heat medium channels 160. When the product drain outlet is open in the direction different from the extending direction of the reaction channels 150, the operator cannot insert the holding member 170 and the like into the respective reaction channels 150 on the product drain side. However, the operator can insert and remove the holding member 170 and the like with respect to the reaction channels 150 on the reaction fluid introduction side appropriately without any inconvenience.

While the respective embodiments have illustrated the heat exchange body 101 as a stacked body in which two kinds of heat transfer bodies having a plate-like shape are stacked, the heat exchange body is not necessarily a stacked body. Since the holding member 170 and the like according to the present disclosure can be removably installed when the reaction channels extending straight are open at least at one end, the present disclosure is applicable to a reactor including a heat exchange body having straight reaction channels such as circular pipes. While the respective embodiments have exemplified the case in which each reaction channel 150 has a rectangular shape in cross section in the direction perpendicular to the flowing direction, the reaction channel 150 may have any shape in cross section.

It should be noted that the present disclosure includes various embodiments which are not disclosed herein. Therefore, the scope of the present disclosure is defined only by the matters according to the claims reasonably derived from the description described above.

What is claimed is:

1. A reactor using heat exchange between a heat medium and a reaction fluid to cause a reaction of the reaction fluid to proceed, the reactor comprising:
    a heat exchange body including a heat medium channel through which the heat medium flows and a reaction channel through which the reaction fluid flows;
    at least one structured catalyst supporting a catalyst for promoting the reaction of the reaction fluid and removably installed in the reaction channel; and
    a holding member including an extending part extending in a direction conforming to an extending direction of the reaction channel and capable of engaging with the at least one structured catalyst, and regulating parts provided in the extending part to regulate a movement of the at least one structured catalyst in the extending direction of the extending part, the holding member being inserted and removed with respect to the reaction channel while holding the at least one structured catalyst.

2. The reactor according to claim 1, wherein the at least one structured catalyst engages with the extending part between a first regulating part of the regulating parts located at a position capable of coming into contact with one side in an extending direction of the at least one structured catalyst and a second regulating part of the regulating parts located at a position capable of coming into contact with another side in the extending direction of the at least one structured catalyst.

3. The reactor according to claim 1, comprising a plurality of structured catalysts each corresponding to the at least one structured catalyst, wherein the extending part engages with the plural structured catalysts arranged in series.

4. The reactor according to claim 1, wherein the extending part is a plate-like member, and the regulating parts are projections projecting in a direction intersecting with the extending direction of the extending part.

5. The reactor according to claim 4, wherein the projections adjacent to each other in the extending direction project in opposite directions.

6. The reactor according to claim 1, wherein the holding member includes an engaging part provided at least at one end of the extending part in the extending direction and brought into contact with an external part of the reaction channel when the at least one structured catalyst is arranged at a predetermined position in the reaction channel.

7. The reactor according to claim 6, further comprising a reference member supported by an external part of the reaction channel and brought into contact with the engaging part.

8. The reactor according to claim 7, wherein the reference member is a stick-like member capable of shifting in a direction different from the extending direction of the reaction channel.

9. The reactor according to claim 7, wherein the reaction channel includes a plurality of branch channels branched in parallel or in layers, and the reference member is brought into contact with the engaging parts of at least two of the holding members installed in the corresponding branch channels.

10. The reactor according to claim 1, wherein the at least one structured catalyst is a corrugated plate-like member having a wave-like shape in cross section holding a part of the extending part.

* * * * *